(12) United States Patent
Xia et al.

(10) Patent No.: US 11,104,734 B2
(45) Date of Patent: Aug. 31, 2021

(54) ANTI-PD-1 MONOCLONAL ANTIBODY

(71) Applicants: Akeso Biopharma, Inc., Guangdong (CN); Taizhou Hanzhong Biopharmaceutics, Inc., Jiangsu (CN)

(72) Inventors: Yu Xia, Guangdong (CN); Baiyong Li, Guangdong (CN); Zhongmin Maxwell Wang, Guangdong (CN); Faming Zhang, Hubei (CN); Gan Xi, Hubei (CN); Ying Huang, Hubei (CN)

(73) Assignees: Akeso Biopharma, Inc., Guangdong (CN); Taizhou Hanzhong Biopharmaceutics, Inc., Jiangsu (CN)

( * ) Notice: Subject to any disclaimer, the term of this patent is extended or adjusted under 35 U.S.C. 154(b) by 0 days.

(21) Appl. No.: 16/146,925

(22) Filed: Sep. 28, 2018

(65) Prior Publication Data

US 2019/0040138 A1    Feb. 7, 2019

Related U.S. Application Data

(63) Continuation of application No. PCT/CN2016/103814, filed on Oct. 28, 2016.

(30) Foreign Application Priority Data

Apr. 1, 2016  (CN) .......................... 201610207741.6

(51) Int. Cl.
 C07K 16/28    (2006.01)

(52) U.S. Cl.
 CPC ...... C07K 16/2818 (2013.01); *C07K 2317/24* (2013.01); *C07K 2317/56* (2013.01); *C07K 2317/565* (2013.01); *C07K 2317/74* (2013.01); *C07K 2317/76* (2013.01); *C07K 2317/92* (2013.01)

(58) Field of Classification Search
 None
 See application file for complete search history.

(56) References Cited

FOREIGN PATENT DOCUMENTS

| CN | 105061597 A | 11/2015 |
|---|---|---|
| CN | 105175544 A | 12/2015 |
| CN | 105238762 A | 1/2016 |
| WO | 2004056875 A1 | 7/2004 |
| WO | 2006121168 A1 | 11/2006 |
| WO | 2011110621 A1 | 9/2011 |
| WO | 2014055648 A1 | 4/2014 |
| WO | 2016014688 A2 | 1/2016 |

OTHER PUBLICATIONS

Skolnick et al. (Trends in Biotechnology 18: 34-39, 2000).*
Greenspan et al. (Nature Biotechnology 7: 936-937, 1999).*
Giusti et al. (Proc. Natl. Acad. Sci. USA. May 1987; 84 (9): 2926-2930).*
Winkler et al (J. Imm., 265:4505-4514, 2000).*
Chien et al. (Proc. Natl. Acad. Sci. USA. Jul. 1989; 86 (14): 5532-5536).*
Caldas et al. (Mol. Immunol. May 2003; 39 (15): 941-952).*
Casadevall et al. (PNAS, vol. 109 No. 31, pp. 12272-12273).*
Extended European Search Report issued for EP patent application No. 16896573.9, dated Oct. 14, 2019.
Notice of Reasons for Refusal issued for JP patent application No. 2019-502126, dated Nov. 19, 2019.
International Search Report issued for international patent application No. PCT/CN2016/103814, dated Feb. 3, 2017.
Written Opinion of the International Searching Authority issued for international patent application No. PCT/CN2016/103814, dated Feb. 3, 2017.
Oral Summons for EP Application No. 16896573 dated Apr. 30, 2021, 7 pages.

* cited by examiner

*Primary Examiner* — Robert A Zeman
(74) *Attorney, Agent, or Firm* — Sheppard Mullin Richter & Hampton LLP

(57) ABSTRACT

Proposed is an anti-PD-1 monoclonal antibody or an antigen binding fragment thereof, comprising a heavy chain variable region having at least one of the amino acid sequences listed below: (1) the amino acid sequence shown in SEQ ID NO: 1; (2) the amino acid sequence shown in SEQ ID NO: 3; (3) the amino acid sequence shown in SEQ ID NO: 5; and (4) an amino acid sequence having more than one conservative amino acid mutation compared with (1)-(3).

6 Claims, 6 Drawing Sheets

Specification includes a Sequence Listing.

SEQUENCE LISTING

```
<160> NUMBER OF SEQ ID NOS: 19

<210> SEQ ID NO 1
<211> LENGTH: 118
<212> TYPE: PRT
<213> ORGANISM: Artificial
<220> FEATURE:
<223> OTHER INFORMATION: amino acid sequence of heavy chain of H1L1

<400> SEQUENCE: 1

Glu Val Gln Leu Val Gln Ser Gly Gly Gly Leu Val Gln Pro Gly Gly
1               5                   10                  15

Ser Leu Lys Leu Ser Cys Ala Ala Ser Gly Phe Thr Phe Ser Ser Tyr
```

```
            20                  25                  30
Gly Met Ser Trp Val Arg Gln Thr Pro Glu Lys Gly Leu Asp Trp Val
        35                  40                  45

Ala Thr Ile Ser Gly Gly Gly Arg Asp Thr Tyr Tyr Pro Asp Ser Val
    50                  55                  60

Lys Gly Arg Phe Thr Ile Ser Arg Asp Asn Ser Lys Asn Asn Leu Tyr
65                  70                  75                  80

Leu Gln Met Asn Ser Leu Arg Ala Glu Asp Thr Ala Leu Tyr Tyr Cys
                85                  90                  95

Ala Arg Gln Lys Gly Glu Ala Trp Phe Ala Tyr Trp Gly Gln Gly Thr
            100                 105                 110

Leu Val Thr Val Ser Ser
            115

<210> SEQ ID NO 2
<211> LENGTH: 111
<212> TYPE: PRT
<213> ORGANISM: Artificial
<220> FEATURE:
<223> OTHER INFORMATION: amino acid sequence of light chain of H1L1

<400> SEQUENCE: 2

Asp Ile Val Leu Thr Gln Ser Pro Ala Ser Leu Ala Val Ser Pro Gly
1               5                   10                  15

Gln Arg Ala Thr Ile Thr Cys Arg Ala Ser Glu Ser Val Asp Asn Tyr
            20                  25                  30

Gly Ile Ser Phe Met Asn Trp Phe Gln Gln Lys Pro Gly Gln Pro Pro
        35                  40                  45

Lys Leu Leu Ile Tyr Ala Ala Ser Asn Lys Gly Thr Gly Val Pro Ala
    50                  55                  60

Arg Phe Ser Gly Ser Gly Ser Gly Thr Asp Phe Thr Leu Asn Ile His
65                  70                  75                  80

Pro Met Glu Glu Asn Asp Thr Ala Met Tyr Phe Cys Gln Gln Ser Lys
                85                  90                  95

Glu Val Pro Trp Thr Phe Gly Gly Gly Thr Lys Leu Glu Ile Lys
            100                 105                 110

<210> SEQ ID NO 3
<211> LENGTH: 118
<212> TYPE: PRT
<213> ORGANISM: Artificial
<220> FEATURE:
<223> OTHER INFORMATION: amino acid sequence of heavy chain of H2L2

<400> SEQUENCE: 3

Glu Val Gln Leu Val Gln Ser Gly Gly Gly Leu Val Gln Pro Gly Gly
1               5                   10                  15

Ser Leu Lys Leu Ser Cys Ala Ala Ser Gly Phe Thr Phe Ser Ser Tyr
            20                  25                  30

Gly Met Ser Trp Val Arg Gln Ala Pro Gly Lys Gly Leu Asp Trp Val
        35                  40                  45

Ala Thr Ile Ser Gly Gly Gly Arg Asp Thr Tyr Tyr Pro Asp Ser Val
    50                  55                  60

Lys Gly Arg Phe Thr Ile Ser Arg Asp Asn Ser Lys Asn Asn Leu Tyr
65                  70                  75                  80

Leu Gln Met Asn Ser Leu Arg Ala Glu Asp Thr Ala Leu Tyr Tyr Cys
                85                  90                  95
```

Ala Arg Gln Lys Gly Glu Ala Trp Phe Ala Tyr Trp Gly Gln Gly Thr
                100                 105                 110

Leu Val Thr Val Ser Ser
        115

<210> SEQ ID NO 4
<211> LENGTH: 111
<212> TYPE: PRT
<213> ORGANISM: Artificial
<220> FEATURE:
<223> OTHER INFORMATION: amino acid sequence of light chain of H2L2

<400> SEQUENCE: 4

Asp Ile Val Leu Thr Gln Ser Pro Ala Ser Leu Ala Val Ser Pro Gly
1               5                   10                  15

Gln Arg Ala Thr Ile Thr Cys Arg Ala Ser Glu Ser Val Asp Asn Tyr
            20                  25                  30

Gly Ile Ser Phe Met Asn Trp Phe Gln Gln Lys Pro Gly Gln Pro Pro
        35                  40                  45

Lys Leu Leu Ile Tyr Ala Ala Ser Asn Lys Gly Thr Gly Val Pro Ala
    50                  55                  60

Arg Phe Ser Gly Ser Gly Ser Gly Thr Asp Phe Thr Leu Asn Ile Asn
65                  70                  75                  80

Pro Met Glu Glu Asn Asp Thr Ala Met Tyr Phe Cys Gln Gln Ser Lys
                85                  90                  95

Glu Val Pro Trp Thr Phe Gly Gly Gly Thr Lys Leu Glu Ile Lys
                100                 105                 110

<210> SEQ ID NO 5
<211> LENGTH: 118
<212> TYPE: PRT
<213> ORGANISM: Artificial
<220> FEATURE:
<223> OTHER INFORMATION: amino acid sequence of heavy chain of H3L3

<400> SEQUENCE: 5

Glu Val Gln Leu Val Gln Ser Gly Gly Gly Leu Val Gln Pro Gly Gly
1               5                   10                  15

Ser Leu Lys Leu Ser Cys Ala Ala Ser Gly Phe Thr Phe Ser Ser Tyr
            20                  25                  30

Gly Met Ser Trp Val Arg Gln Ala Pro Gly Lys Gly Leu Asp Trp Val
        35                  40                  45

Ala Thr Ile Ser Gly Gly Gly Arg Asp Thr Tyr Tyr Pro Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gln Lys Gly Glu Ala Trp Phe Ala Tyr Trp Gly Gln Gly Thr
                100                 105                 110

Leu Val Thr Val Ser Ser
        115

<210> SEQ ID NO 6
<211> LENGTH: 111
<212> TYPE: PRT
<213> ORGANISM: Artificial
<220> FEATURE:
<223> OTHER INFORMATION: amino acid sequence of light chain of H3L3

-continued

<400> SEQUENCE: 6

Asp Ile Val Leu Thr Gln Ser Pro Ala Ser Leu Ala Val Ser Pro Gly
1               5                   10                  15

Gln Arg Ala Thr Ile Thr Cys Arg Ala Ser Glu Ser Val Asp Asn Tyr
            20                  25                  30

Gly Ile Ser Phe Met Asn Trp Tyr Gln Gln Lys Pro Gly Gln Pro Pro
        35                  40                  45

Lys Leu Leu Ile Tyr Ala Ala Ser Asn Lys Ala Thr Gly Val Pro Ala
    50                  55                  60

Arg Phe Ser Gly Ser Gly Ser Gly Thr Asp Phe Thr Leu Asn Ile Asn
65                  70                  75                  80

Pro Met Glu Ala Asn Asp Thr Ala Val Tyr Phe Cys Gln Gln Ser Lys
                85                  90                  95

Glu Val Pro Trp Thr Phe Gly Gly Gly Thr Lys Leu Glu Ile Lys
            100                 105                 110

<210> SEQ ID NO 7
<211> LENGTH: 354
<212> TYPE: DNA
<213> ORGANISM: Artificial
<220> FEATURE:
<223> OTHER INFORMATION: nucleotide sequence of heavy chain of H1L1

<400> SEQUENCE: 7
gaagtgcagc tggtgcagag cggaggggga ctggtgcagc ccggcgggtc tctgaagctg      60
agttgcgccg cttcaggatt cacttttagc tcctacggca tgtcctgggt gcgacagacc     120
cccgagaaag gctggactg gtcgctacc atctctggag gcgggagaga cacatactat       180
cctgatagtg tcaagggccg gttcacaatt agcagagaca actccaaaaa caatctgtat     240
ctgcagatga atagcctgag gcagaagat accgccctgt actattgtgc cgccagaaa       300
ggagaggctt ggtttgcata ctggggacag gggacactgg tcaccgtcag cagc           354

<210> SEQ ID NO 8
<211> LENGTH: 354
<212> TYPE: DNA
<213> ORGANISM: Artificial
<220> FEATURE:
<223> OTHER INFORMATION: nucleotide sequence of heavy chain of H2L2

<400> SEQUENCE: 8
gaggtgcagc tggtgcagtc tggcggcgga ctggtgcagc ccggcgggtc actgaagctg      60
agctgcgccg cttccggctt caccttagc tcctacggaa tgtcctgggt gcgacaggca      120
cccgggaagg gctggactg gtcgctact atctcaggag gcgggagaga cacctactat       180
cctgatagcg tcaagggccg gttcacaatt agccgggaca acagcaagaa caatctgtac     240
ctgcagatga acagcctgag gctgaggat actgcactgt actattgtgc cgccagaag       300
ggcgaagcat ggtttgccta ttggggccag ggaaccctgg tgacagtctc tagt           354

<210> SEQ ID NO 9
<211> LENGTH: 354
<212> TYPE: DNA
<213> ORGANISM: Artificial
<220> FEATURE:
<223> OTHER INFORMATION: nucleotide sequence of heavy chain of H3L3

<400> SEQUENCE: 9
gaggtgcagc tggtgcagag tggaggcggg ctggtgcagc ccggcgggtc actgaagctg      60

```
agctgcgccg cttccggctt cacctttagc tcctacggaa tgtcctgggt gcgacaggca    120
cccgggaagg ggctggactg ggtcgctact atctcaggag gcgggagaga cacctactat    180
cctgatagcg tgaagggccg gttcacaatt agccgggaca acagcaagaa cactctgtac    240
ctgcagatga actctctgag ggctgaggat acagcagtct actattgtgc cgccagaaag    300
ggcgaagcat ggtttgccta ttggggccag ggaaccctgg tgacagtctc tagt           354
```

```
<210> SEQ ID NO 10
<211> LENGTH: 333
<212> TYPE: DNA
<213> ORGANISM: Artificial
<220> FEATURE:
<223> OTHER INFORMATION: nucleotide sequence of light chain of H1L1

<400> SEQUENCE: 10
gatattgtgc tgactcagag ccctgcttcc ctggccgtgt ctccaggaca gcgagctacc     60
atcacatgca gagcatctga gagtgtggac aactacggaa ttagtttcat gaattggttt    120
cagcagaagc ccggccagcc ccctaaactg ctgatctatg ccgctagcaa caagggcacc    180
ggggtgcctg ctcgattctc aggaagcggc tccgggacag actttactct gaacattcac    240
ccaatggagg aaaatgatac agcaatgtac ttctgccagc agagcaagga ggtgccctgg    300
acctttggcg ggggaacaaa gctggaaatc aaa                                  333
```

```
<210> SEQ ID NO 11
<211> LENGTH: 333
<212> TYPE: DNA
<213> ORGANISM: Artificial
<220> FEATURE:
<223> OTHER INFORMATION: nucleotide sequence of light chain of H2L2

<400> SEQUENCE: 11
gatattgtgc tgactcagag ccctgcttcc ctggccgtgt ctccaggaca gcgagctacc     60
atcacatgca gagcatctga gagtgtggac aactacggaa ttagtttcat gaattggttt    120
cagcagaagc ccggccagcc ccctaaactg ctgatctatg ccgctagcaa caagggcacc    180
ggggtgcctg ctcgattctc aggaagcggc tccgggacag actttactct gaacattaac    240
ccaatggagg aaaatgatac agcaatgtac ttctgccagc agagcaagga ggtgccctgg    300
acctttggcg ggggaacaaa gctggaaatc aaa                                  333
```

```
<210> SEQ ID NO 12
<211> LENGTH: 333
<212> TYPE: DNA
<213> ORGANISM: Artificial
<220> FEATURE:
<223> OTHER INFORMATION: nucleotide sequence of light chain of H3L3

<400> SEQUENCE: 12
gacatcgtcc tgactcagag ccctgcttcc ctggccgtga gcccaggcca gcgagcaacc     60
atcacatgca gagcctcaga gagcgtggac aactacggca ttagcttcat gaattggtat    120
cagcagaagc ccgggcagcc tcccaagctg ctgatctacg ccgcttccaa caaggccact    180
ggggtgcctg ctcgattctc cggctctggg agtggaacag actttactct gaacattaat    240
ccaatggaag ctaatgatac agcagtgtat ttctgccagc agagcaagga ggtcccatgg    300
accttcggcg gcggcaccaa gctggagatc aag                                  333
```

```
<210> SEQ ID NO 13
<211> LENGTH: 422
```

<212> TYPE: PRT
<213> ORGANISM: Artificial
<220> FEATURE:
<223> OTHER INFORMATION: fusion protein PD-1-mIgGFc

<400> SEQUENCE: 13

```
Met Gln Ile Pro Gln Ala Pro Trp Pro Val Val Trp Ala Val Leu Gln
 1               5                  10                  15

Leu Gly Trp Arg Pro Gly Trp Phe Leu Asp Ser Pro Asp Arg Pro Trp
            20                  25                  30

Asn Pro Pro Thr Phe Ser Pro Ala Leu Leu Val Val Thr Glu Gly Asp
        35                  40                  45

Asn Ala Thr Phe Thr Cys Ser Phe Ser Asn Thr Ser Glu Ser Phe Val
 50                  55                  60

Leu Asn Trp Tyr Arg Met Ser Pro Ser Asn Gln Thr Asp Lys Leu Ala
 65                  70                  75                  80

Ala Phe Pro Glu Asp Arg Ser Gln Pro Gly Gln Asp Cys Arg Phe Arg
                85                  90                  95

Val Thr Gln Leu Pro Asn Gly Arg Asp Phe His Met Ser Val Val Arg
            100                 105                 110

Ala Arg Arg Asn Asp Ser Gly Thr Tyr Leu Cys Gly Ala Ile Ser Leu
        115                 120                 125

Ala Pro Lys Ala Gln Ile Lys Glu Ser Leu Arg Ala Glu Leu Arg Val
130                 135                 140

Thr Glu Arg Arg Ala Glu Val Pro Thr Ala His Pro Ser Pro Ser Pro
145                 150                 155                 160

Arg Pro Ala Gly Gln Phe Gln Thr Leu Val Ser Pro Arg Pro Ser Glu
                165                 170                 175

Thr Val Thr Cys Asn Val Ala His Pro Ala Ser Ser Thr Lys Val Asp
            180                 185                 190

Lys Lys Ile Val Pro Arg Asp Cys Gly Cys Lys Pro Cys Ile Cys Thr
        195                 200                 205

Val Pro Glu Val Ser Ser Val Phe Ile Phe Pro Pro Lys Pro Lys Asp
210                 215                 220

Val Leu Thr Ile Thr Leu Thr Pro Lys Val Thr Cys Val Val Val Asp
225                 230                 235                 240

Ile Ser Lys Asp Asp Pro Glu Val Gln Phe Ser Trp Phe Val Asp Asp
                245                 250                 255

Val Glu Val His Thr Ala Gln Thr Gln Pro Arg Glu Glu Gln Phe Asn
            260                 265                 270

Ser Thr Phe Arg Ser Val Ser Glu Leu Pro Ile Met His Gln Asp Trp
        275                 280                 285

Leu Asn Gly Lys Glu Phe Lys Cys Arg Val Asn Ser Ala Ala Phe Pro
290                 295                 300

Ala Pro Ile Glu Lys Thr Ile Ser Lys Thr Lys Gly Arg Pro Lys Ala
305                 310                 315                 320

Pro Gln Val Tyr Thr Ile Pro Pro Lys Glu Gln Met Ala Lys Asp
                325                 330                 335

Lys Val Ser Leu Thr Cys Met Ile Thr Asp Phe Phe Pro Glu Asp Ile
            340                 345                 350

Thr Val Glu Trp Gln Trp Asn Gly Gln Pro Ala Glu Asn Tyr Lys Asn
        355                 360                 365

Thr Gln Pro Ile Met Asn Thr Asn Gly Ser Tyr Phe Val Tyr Ser Lys
370                 375                 380
```

```
Leu Asn Val Gln Lys Ser Asn Trp Glu Ala Gly Asn Thr Phe Thr Cys
385                 390                 395                 400

Ser Val Leu His Glu Gly Leu His Asn His Thr Glu Lys Ser Leu
                405                 410                 415

Ser His Ser Pro Gly Lys
            420

<210> SEQ ID NO 14
<211> LENGTH: 8
<212> TYPE: PRT
<213> ORGANISM: Artificial
<220> FEATURE:
<223> OTHER INFORMATION: CDR1 of heavy chain

<400> SEQUENCE: 14

Gly Phe Thr Phe Ser Ser Tyr Gly
1               5

<210> SEQ ID NO 15
<211> LENGTH: 8
<212> TYPE: PRT
<213> ORGANISM: Artificial
<220> FEATURE:
<223> OTHER INFORMATION: CDR2 of heavy chain

<400> SEQUENCE: 15

Ile Ser Gly Gly Gly Arg Asp Thr
1               5

<210> SEQ ID NO 16
<211> LENGTH: 11
<212> TYPE: PRT
<213> ORGANISM: Artificial
<220> FEATURE:
<223> OTHER INFORMATION: CDR3 of heavy chain

<400> SEQUENCE: 16

Ala Arg Gln Lys Gly Glu Ala Trp Phe Ala Tyr
1               5                   10

<210> SEQ ID NO 17
<211> LENGTH: 10
<212> TYPE: PRT
<213> ORGANISM: Artificial
<220> FEATURE:
<223> OTHER INFORMATION: CDR1 of light chain

<400> SEQUENCE: 17

Glu Ser Val Asp Asn Tyr Gly Ile Ser Phe
1               5                   10

<210> SEQ ID NO 18
<211> LENGTH: 3
<212> TYPE: PRT
<213> ORGANISM: Artificial
<220> FEATURE:
<223> OTHER INFORMATION: CDR2 of light chain

<400> SEQUENCE: 18

Ala Ala Ser
1

<210> SEQ ID NO 19
<211> LENGTH: 9
<212> TYPE: PRT
<213> ORGANISM: Artificial
```

```
<220> FEATURE:
<223> OTHER INFORMATION: CDR3 of light chain

<400> SEQUENCE: 19

Gln Gln Ser Lys Glu Val Pro Trp Thr
1               5
```

ANTI-PD-1 MONOCLONAL ANTIBODY

CROSS-REFERENCE TO RELATED APPLICATION

The application is a continuation application based on PCT Application No. PCT/CN2016/103814 filed on Oct. 28, 2016, which claims a priority to and benefits of Chinese Patent Applications No. 201610207741.6, filed with the State Intellectual Property Office of P. R. China on Apr. 1, 2016, the entire contents of which are incorporated herein by reference.

FIELD

The present disclosure relates to the field of biomedicine, more particular to a monoclonal antibody against PD-1.

BACKGROUND

Programmed death factor 1 (PD-1) (also known as CD279, Gene ID: PDCD1, Genebank accession No: NP_005009), as an inhibitory member of the immunoglobulin superfamily with homology to CD28, is a cell surface receptor critical in the regulation of balance between stimulatory and inhibitory signals in the immune system as well maintenance of peripheral tolerance. PD-1 is a monomeric type I transmembrane protein, consisting of an immunoglobulin variable region-like extracellular domain and a cytoplasmic domain with an immunoreceptor tyrosine-based inhibition motif (ITIM) and an immunoreceptor tyrosine-based switch motif (ITSM). The expression of PD-1 is inducible on T cells, B cells, natural killer (NK) cells and monocytes, for example after activation of lymphocytes via signal transduction of T cell receptor (TCR) or B cell receptor (BCR). PD-1 has two known ligands, i.e. PD-L1 (such as, B7-H1, CD274) and PD-L2 (such as, B7-DC, CD273), which are members of the B7 family expressed on the cell surface. When ligating a ligand, PD-1 recruits phosphatases (such as SHP-1 and SHP-2) to its intracellular tyrosine motif, which subsequently dephosphorylates effector molecules activated via signal transduction of TCR or BCR. Thus, PD-1 is capable of transducing inhibitory signals into T cells and B cells only when linked with TCR or BCR at same time.

However, there still exists a need to improve antibody specifically recognizing PD-1.

SUMMARY

Embodiments of the present disclosure aim to solve at least one of the problems existing in the related art to at least some extent, or to at least provide a useful commercial alternative. For this purpose, the present disclosure provides in embodiments a monoclonal antibody against programmed death-1 (PD-1).

In one aspect, the present disclosure in embodiments provides a monoclonal antibody against PD-1 or antigen-binding fragment thereof. In some embodiments, the antibody or antigen-binding fragment thereof includes a heavy chain variable region having at least one of amino acid sequences consisting of: (1) the amino acid sequence of SEQ ID NO: 1, (2) the amino acid sequence of SEQ ID NO: 3, (3) the amino acid sequence of SEQ ID NO: 5, and (4) an amino acid sequence having one or more conservative amino acid mutations compared to (1) to (3).

In some embodiments, the antibody or antigen-binding fragment thereof further includes a light chain variable region having at least one of amino acid sequences consisting of: (5) the amino acid sequence of SEQ ID NO: 2, (6) the amino acid sequence of SEQ ID NO: 4, (7) the amino acid sequence of SEQ ID NO: 6, and (8) an amino acid sequence having one or more conservative amino acid mutations compared to (5) to (7).

In an embodiment, the antibody or antigen-binding fragment thereof includes a heavy chain variable region having the amino acid sequence of SEQ ID NO: 1 (EVQLVQSGG-GLVQPGGSLKLSCAASGFTFSSYGMSWVRQT-PEKGLDWVATISGGGRDT YYPDSVKGRFTIS-RDNSKNNLYLQMNSLRAEDTALYYCARQKGEAWFA YWGQGTLVTV SS), and a light chain variable region having the amino acid sequence of SEQ ID NO: 2 (DI-VLTQSPASLAVSPGQRATITCRASESVDNYGIS-FMNWFQQKPGQPPKLLIYAASNKGT GVPARFSGSGSGTDFTLNIHPMEEND-TAMYFCQQSKEVPWTFGGGTKLEIK).

In another embodiment, the antibody or antigen-binding fragment thereof includes a heavy chain variable region having the amino acid sequence of SEQ ID NO: 3 (EVQLVQSGGGLVQPGGSLKLS-CAASGFTFSSYGMSWVRQAPGKGLDWVATISGG-GRDT YYPDSVKGRFTISRDNSKNNLYLQMNSLRAE-DTALYYCARQKGEAWFAYWGQGTLVTV SS), and a light chain variable region having the amino acid sequence of SEQ ID NO: 4 (DIVLTQSPASLAVSPGQRATITCRAS-ESVDNYGISFMNWFQQKPGQPPKLLIYAASNKGT GVPARFSGSGSGTDFTLNINPMEEND-TAMYFCQQSKEVPWTFGGGTKLEIK).

In still another embodiment, the antibody or antigen-binding fragment thereof includes a heavy chain variable region having the amino acid sequence of SEQ ID NO: 5 (EVQLVQSGGGLVQPGGSLKLS-CAASGFTFSSYGMSWVRQAPGKGLDWVATISGG-GRDT YYPDSVKGRFTISRDNSKNTLYLQMNSLRAE-DTAVYYCARQKGEAWFAYWGQGTLVTV SS), and a light chain variable region having the amino acid sequence of SEQ ID NO: 6 (DIVLTQSPASLAVSPGQRATITCRAS-ESVDNYGISFMNWYQQKPGQPPKLLIYAASNKAT GVPARFSGSGSGTDFTLNINPMEAND-TAVYFCQQSKEVPWTFGGGTKLEIK).

In some embodiments, the antibody or antigen-binding fragment thereof is a monoclonal antibody.

In some embodiments, the antibody or antigen-binding fragment thereof specifically binds to PD-1 in an efficient manner, as well is capable of promoting the activation and proliferation of T cells, regulating the expression and secretion of cytokines, or stimulating anti-tumor cells to generate a stronger immune response.

It is surprisingly found by present inventors that the antibody or antigen-binding fragment thereof in embodiments of the present disclosure is capable of specifically recognizing PD-1, as well promoting the activation and proliferation of T cells, regulating the expression and secretion of cytokines, or stimulating anti-tumor cells to generate a stronger immune response.

In another aspect, the present disclosure in embodiments provides an isolated polynucleotide. In some embodiments, the polynucleotide encodes the antibody or antigen-binding fragment thereof described in the above.

In some embodiments, the polynucleotide described in the above includes at least one of nucleotide sequences as follows.

In a specific embodiment, the polynucleotide includes the nucleotide sequence of SEQ ID NO: 7 or complementary sequence thereof, wherein the nucleotide sequence of SEQ ID NO: 7 encodes the amino acid sequence of SEQ ID NO: 1 (i.e. an amino acid of the heavy chain variable region of H1L1 antibody).

(SEQ ID NO: 7)
GAAGTGCAGCTGGTGCAGAGCGGAGGGGGACTGGTGCAGCCCGGCGGGT

CTCTGAAGCTGAGTTGCGCCGCTTCAGGATTCACTTTTAGCTCCTACGG

CATGTCCTGGGTGCGACAGACCCCCGAGAAAGGGCTGGACTGGGTCGCT

ACCATCTCTGGAGGCGGGAGAGACACATACTATCCTGATAGTGTCAAGG

GCCGGTTCACAATTAGCAGAGACAACTCCAAAAACAATCTGTATCTGCA

GATGAATAGCCTGAGGGCAGAAGATACCGCCCTGTACTATTGTGCCCGC

CAGAAAGGAGAGGCTTGGTTTGCATACTGGGGACAGGGGACACTGGTCA

CCGTCAGCAGC

In another specific embodiment, the polynucleotide includes the nucleotide sequence of SEQ ID NO: 8 or complementary sequence thereof, wherein the nucleotide sequence of SEQ ID NO: 8 encodes the amino acid sequence of SEQ ID NO: 3 (i.e. an amino acid of the heavy chain variable region of H2L2 antibody).

(SEQ ID NO: 8)
GAGGTGCAGCTGGTGCAGTCTGGCGGCGGACTGGTGCAGCCCGGCGGGT

CACTGAAGCTGAGCTGCGCCGCTTCCGGCTTCACCTTTAGCTCCTACGG

AATGTCCTGGGTGCGACAGGCACCCGGGAAGGGGCTGGACTGGGTCGCT

ACTATCTCAGGAGGCGGGAGAGACACCTACTATCCTGATAGCGTCAAGG

GCCGGTTCACAATTAGCCGGGACAACAGCAAGAACAATCTGTACCTGCA

GATGAACAGCCTGAGGGCTGAGGATACTGCACTGTACTATTGTGCCCGC

CAGAAGGGCGAAGCATGGTTTGCCTATTGGGGCCAGGGAACCCTGGTGA

CAGTCTCTAGT

In still another specific embodiment, the polynucleotide includes the nucleotide sequence of SEQ ID NO: 9 or complementary sequence thereof, wherein the nucleotide sequence of SEQ ID NO: 9 encodes the amino acid sequence of SEQ ID NO: 5 (i.e. an amino acid of the heavy chain variable region of H3L3 antibody).

(SEQ ID NO: 9)
GAGGTGCAGCTGGTGCAGAGTGGAGGCGGGCTGGTGCAGCCCGGCGGGT

CACTGAAGCTGAGCTGCGCCGCTTCCGGCTTCACCTTTAGCTCCTACGG

AATGTCCTGGGTGCGACAGGCACCCGGGAAGGGGCTGGACTGGGTCGCT

ACTATCTCAGGAGGCGGGAGAGACACCTACTATCCTGATAGCGTGAAGG

GCCGGTTCACAATTAGCCGGGACAACAGCAAGAACACTCTGTACCTGCA

GATGAACTCTCTGAGGGCTGAGGATACAGCAGTCTACTATTGTGCCCGC

CAGAAGGGCGAAGCATGGTTTGCCTATTGGGGCCAGGGAACCCTGGTGA

CAGTCTCTAGT

In a further specific embodiment, the polynucleotide includes the nucleotide sequence of SEQ ID NO: 10 or complementary sequence thereof, wherein the nucleotide sequence of SEQ ID NO: 10 encodes the amino acid sequence of SEQ ID NO: 2 (i.e. an amino acid of the light chain variable region of the H1L1 antibody).

(SEQ ID NO: 10)
GATATTGTGCTGACTCAGAGCCCTGCTTCCCTGGCCGTGTCTCCAGGAC

AGCGAGCTACCATCACATGCAGAGCATCTGAGAGTGTGGACAACTACGG

AATTAGTTTCATGAATTGGTTTCAGCAGAAGCCCGGCCAGCCCCCTAAA

CTGCTGATCTATGCCGCTAGCAACAAGGGCACCGGGGTGCCTGCTCGAT

TCTCAGGAAGCGGCTCCGGGACAGACTTTACTCTGAACATTCACCCAAT

GGAGGAAAATGATACAGCAATGTACTTCTGCCAGCAGAGCAAGGAGGTG

CCCTGGACCTTTGGCGGGGGAACAAAGCTGGAAATCAAA

In a further specific embodiment, the polynucleotide includes the nucleotide sequence of SEQ ID NO: 11 or complementary sequence thereof, wherein the nucleotide sequence of SEQ ID NO: 11 encodes the amino acid sequence of SEQ ID NO: 4 (i.e. an amino acid of the light chain variable region of the H2L2 antibody).

(SEQ ID NO: 11)
GATATTGTGCTGACTCAGAGCCCTGCTTCCCTGGCCGTGTCTCCAGGAC

AGCGAGCTACCATCACATGCAGAGCATCTGAGAGTGTGGACAACTACGG

AATTAGTTTCATGAATTGGTTTCAGCAGAAGCCCGGCCAGCCCCCTAAA

CTGCTGATCTATGCCGCTAGCAACAAGGGCACCGGGGTGCCTGCTCGAT

TCTCAGGAAGCGGCTCCGGGACAGACTTTACTCTGAACATTAACCCAAT

GGAGGAAAATGATACAGCAATGTACTTCTGCCAGCAGAGCAAGGAGGTG

CCCTGGACCTTTGGCGGGGGAACAAAGCTGGAAATCAAA

In a further specific embodiment, the polynucleotide includes the nucleotide sequence of SEQ ID NO: 12 or complementary sequence thereof, wherein the nucleotide sequence of SEQ ID NO: 12 encodes the amino acid sequence of SEQ ID NO: 6 (i.e. an amino acid of the light chain variable region of the H3L3 antibody).

(SEQ ID NO: 12)
GACATCGTCCTGACTCAGAGCCCTGCTTCCCTGGCCGTGAGCCCAGGCC

AGCGAGCAACCATCACATGCAGAGCCTCAGAGAGCGTGGACAACTACGG

CATTAGCTTCATGAATTGGTATCAGCAGAAGCCCGGGCAGCCTCCCAAG

CTGCTGATCTACGCCGCTTCCAACAAGGCCACTGGGGTGCCTGCTCGAT

TCTCCGGCTCTGGGAGTGGAACAGACTTTACTCTGAACATTAATCCAAT

GGAAGCTAATGATACAGCAGTGTATTTCTGCCAGCAGAGCAAGGAGGTC

CCATGGACCTTCGGCGGCGGCACCAAGCTGGAGATCAAG

It is found by the present inventors that it is possible to synthesize the antibody or antigen-binding fragment thereof specifically recognizing PD-1 in embodiments of the present disclosure by using the polynucleotide according to embodiments of the present disclosure. The features and advantages of such the antibody or antigen-binding fragment thereof specifically binding to PD-1 described in the above are also suitable for the polynucleotide, which will not be described in detail.

In still another aspect, the present disclosure in embodiments provides an expression vector, including the polynucleotide described in the above.

In a specific embodiment, the expression vector further includes:

a control element, operably connected to the polynucleotide and configured to control the expression of the polynucleotide in a host cell.

In a specific embodiment, the host cell can be a mammalian cell, further the mammalian cell can be a human renal epithelial cell line cell.

In a specific embodiment, the human renal epithelial cell line is 293T cells.

In a specific embodiment, the control element includes at least one of: a promoter, an enhancer and a terminator, optionally, the promoter is a cytomegalovirus (CMV) promoter, the enhancer is an early CMV enhancer, and the terminator is an SV polyA terminator.

In a specific embodiment, the control element includes a cytomegalovirus promoter, an early CMV enhancer and an SV polyA terminator.

In yet another aspect, the present disclosure in embodiments provides a recombinant cell, including the expression vector described in the above.

In yet another aspect, the present disclosure in embodiments provides a method for preparing the antibody or antigen-binding fragment thereof described in the above, including culturing the recombinant cell described in the above.

It is found by the present inventors that it is possible to efficiently synthesize the antibody or antigen-binding fragment thereof specifically recognizing PD-1 in embodiments of the present disclosure by culturing the recombinant cell described in the above according to the present method. The features and advantages of such the antibody or antigen-binding fragment thereof specifically binding to PD-1 described in the above are also suitable for the method, which will not be described in detail.

In yet another aspect, the present disclosure in embodiments provides use of the polynucleotide, the expression vector or the recombinant cell described in the above in the preparation of an antibody or antigen-binding fragment thereof, wherein the antibody specifically binds to PD-1. Thus, it is found by the present inventors that it is possible to efficiently prepare and acquire the antibody or antigen-binding fragment thereof capable of specifically binding to PD-1 by using the polynucleotide, the expression vector or the recombinant cell described in the above. Further, with the antibody or antigen-binding fragment thereof prepared, it is possible to block the binding of PD-1 to receptor thereof effectively, thus further blocking corresponding signaling pathways of PD-1 receptors (such as SHP1/2), thereby inhibiting growth of tumor effectively.

In yet another aspect, the present disclosure in embodiments provides a hybridoma, deposited in the China Center for Type Culture Collection (CCTCC).

It is found by the present inventors that it is possible to efficiently synthesize the antibody or antigen-binding fragment thereof specifically recognizing PD-1 in embodiments of the present disclosure by using the hybridoma according to embodiments of the present disclosure. The features and advantages of such the antibody or antigen-binding fragment thereof specifically binding to PD-1 described in the above are also suitable for the hybridoma, which will not be described in detail.

In yet another aspect, the present disclosure in embodiments provides use of the hybridoma described in the above in the preparation of a monoclonal antibody.

It is found by the present inventors that it is possible to efficiently synthesize the antibody or antigen-binding fragment thereof specifically recognizing PD-1 in embodiments of the present disclosure by using the hybridoma according to embodiments of the present disclosure. The features and advantages of such the antibody or antigen-binding fragment thereof specifically binding to PD-1 described in the above are also suitable for the use, which will not be described in detail.

In yet another aspect, the present disclosure in embodiments provides use of the antibody or antigen-binding fragment thereof, as well the polynucleotide, the expression vector, the recombinant cell or the hybridoma described in the above in the preparation of a medicament for promoting the activation and proliferation of T cells, regulating the expression and secretion of cytokines, or stimulating antitumor cells to generate a stronger immune response.

In yet another aspect, the present disclosure in embodiments provides a pharmaceutical composition. In some embodiments, the pharmaceutical composition includes the antibody or antigen-binding fragment thereof, the polynucleotide, the expression vector, the recombinant cell or the hybridoma described in the above.

In yet another aspect, the present disclosure in embodiments provides a method for identifying a medicament capable of binding to PD-1. In some embodiments, the method includes:

contacting the antibody or antigen-binding fragment thereof described in the above with an antigen in the presence of a candidate, and determining a first binding amount of the antibody or antigen-binding fragment thereof to the antigen, wherein the antigen is PD-1 or fragment thereof; and contacting the antibody or antigen-binding fragment thereof described in the above with an antigen in the absence of the candidate, and determining a second binding amount of the antibody or antigen-binding fragment thereof to the antigen, wherein the antigen is PD-1 or fragment thereof, wherein the second binding amount higher than the first binding amount is an indication that the candidate is capable of binding to PD-1.

Thus, it is possible to screen the candidate binding to PD-1 according to the present method.

In yet another aspect, the present disclosure in embodiments provides a drug combination. In some embodiments, the drug combination includes:

(1) the antibody or antigen-binding fragment thereof, the polynucleotide, the expression vector, the recombinant cell or the hybridoma described in the above; and (2) an immune-enhancing agent different from (1).

In some embodiments, the immune-enhancing agent different from (1) includes at least one selected from the group consisting of: an anti-cytotoxic T lymphocyte antigen 4 (CTLA-4) antibody, an anti-CD40 antibody, Budesonide and a salicylate, optionally the salicylate includes at least one of sulfasalazine, olsalazine, balsalazide and mesalamine.

Blocking both PD-1 and CTLA-4 is normally applied in combination with the standard tumor therapy (e.g., chemotherapy). It is demonstrated by clinical trials that same efficacy can be achieved by a chemotherapeutic drug with a reduced dosage when used in combination with both anti-PD-1 antibody and anti-CTLA-4 antibody. It is reported in literatures that Decarbazine (Docetaxel, an anticancer drug)

or interleukin-2 (IL-2) in combination with both anti-PD-1 antibody and anti-CTLA-4 antibody is useful in treatment of melanoma. On one hand, the chemotherapeutic drug induces cell death, which in turn increases the level of antigens expressed by the tumor cells. On the other hand, the combined blockade of PD-1 and CTLA-4 enhances the synergistic effect among radiation therapy, surgery, hormone therapy and the like, each of which enlarges sources of the antigens in the body. Further, angiogenesis inhibitors can also be used in combination with both anti-PD-1 antibody and anti-CTLA-4 antibody to inhibit vascular proliferation, thereby further inhibiting tumor cell growth, which may also be contributed to the increased expression of the antigen in the body.

The additional aspects and advantages of the present disclosure will be set forth partly in the following description, part of which will become apparent from the description or understood from the practice of the present disclosure.

BRIEF DESCRIPTION OF THE DRAWINGS

The above and/or additional aspects and advantages of the present disclosure will become apparent and readily understood from the description of examples in combination with the following figures, in which.

DETAILED DESCRIPTION

Figure 1:
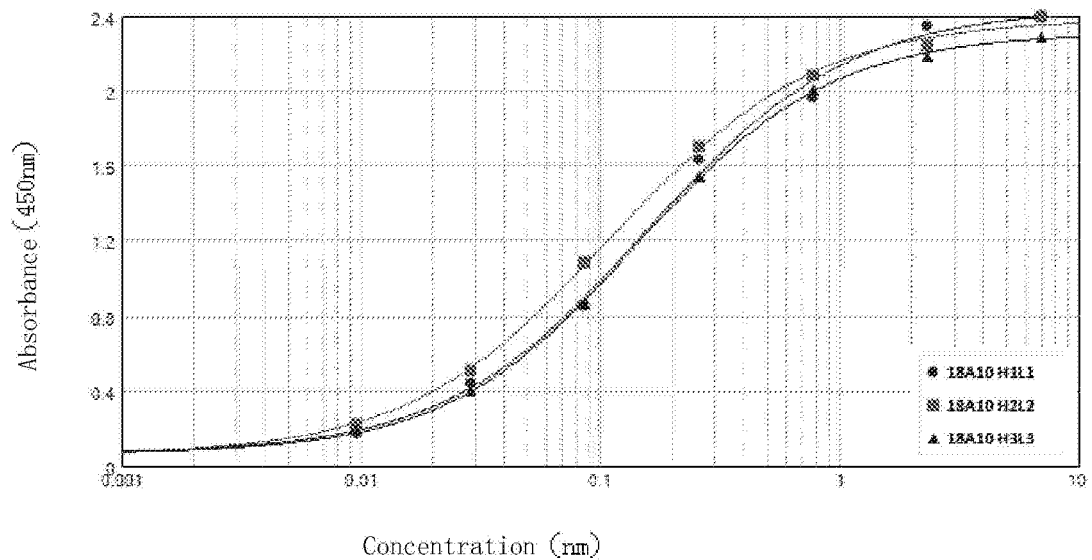
FIG. 1 is a graph showing ELISA results of H1L1, H2L2 and H3L3 antibodies binding to PD-1 according to an embodiment of the present disclosure.

The examples of the present disclosure are described in detail below. It should be noted that such examples are explanatory, and aim to explain the present disclosure rather than to be construed to limit the present disclosure. If not explicitly specified, the reagents used in the following examples are commercially available or may be synthesized according to the description of the present disclosure or known techniques or conditions. Reaction conditions not listed are easily available to those skilled in the art.

EXAMPLE 1

Establishment of PD-1 4G10 Hybridoma Cell Line

PD-1-mIgGFc fusion protein having the following amino acid sequence was prepared according to biological methods.

(SEQ ID NO: 13)
MQIPQAPWPVVWAVLQLGWRPGWFLDSPDRPWNPPTFSPALLVVTEGDN

ATFTCSFSNTSESFVLNWYRMSPSNQTDKLAAFPEDRSQPGQDCRFRVT

QLPNGRDFHMSVVRARRNDSGTYLCGAISLAPKAQIKESLRAELRVTER

RAEVPTAHPSPSPRPAGQFQTLVSPRPSETVTCNVAHPASSTKVDKKIV

PRDCGCKPCICTVPEVSSVFIFPPKPKDVLTITLTPKVTCVVVDISKDD

PEVQFSWFVDDVEVHTAQTQPREEQFNSTFRSVSELPIMHQDWLNGKEF

KCRVNSAAFPAPIEKTISKTKGRPKAPQVYTIPPPKEQMAKDKVSLTCM

ITDFFPEDITVEWQWNGQPAENYKNTQPIMNTNGSYFVYSKLNVQKSNW

EAGNTFTCSVLHEGLHNHHTEKSLSHSPGK.

Step 1 Mouse Immunization and Cell Fusion

BALB/C mice were immunized with the antigen (i.e., the PD-1-mIgGFc fusion protein prepared as above) which was emulsified with Freund's adjuvant in advance. After induction of immune responses in the BALB/C mice, splenocytes were harvested and fused with murine myeloma cells, thus obtaining hybridoma cells, which were further cultured in a 96-well plate individually.

Step 2 Indirect ELISA

The hybridoma cells secreting individual new antibodies capable of specific binding to PD-1 were screened by indirect ELISA with an ELISA plate coated with antigen (PD-1-hFc) and blocked with 1% BSA in the PBS buffer.

Specifically, the indirect ELISA was conducted as follows.

Step 2.1 Antigen Coating

An ELISA plate was coated with PD-1-hFc antigen in a concentration of 1μg/ml (50 μl per well) by incubation at 4° C. overnight.

Step 2.2 Blocking

The ELISA plate coated with the PD-1-hFc antigen was blocked with 1% BSA in the PBS buffer at 37° C. for 2 hours, and washed with 1×PBST buffer containing 1% Tween-20 for three times, with gently patting to dryness.

Step 2.3 Incubation with Primary Antibody

The antibody, secreted by individual hybridoma cells, was diluted from 1μg/ml in series by 1:3, with 7 gradient antibody solutions obtained. The 7 gradient antibody solutions and the blank PBS control were respectively added into the blocked ELISA plate for incubation at 37° C. for 1 hour.

Step 2.4 Incubation with Secondary Antibody

After the ELISA plate was washed with the PBST buffer for three times and gently patted to dryness, goat anti-mouse IgG-HRP (H+L) as a secondary antibody in 1:5000 dilution (50 μl per well) was added for incubation at 37° C. for 1 hour.

Step 2.5 Developing

After the ELISA plate was washed with the PBST buffer for three times and gently patted to dryness again, 3,3',5,5'-

Tetramethylbenzidine (TMB) as a developer in 50 µl per well was added for incubation at room temperature for 5 to 10 minutes.

Step 2.6 Termination of Developing

2M $H_2SO_4$ solution in 50 µl per well was added to terminate developing.

Step 2.7 Reading

The absorbance of solution in each well was measured with the microplate reader under a wavelength of 450 nm.

Step 3 Competitive ELISA

By the indirect ELISA, those selected hybridoma cells were further screened by the competitive ELISA for those secreting monoclonal antibodies competitively binding to PD-1 in the presence of PD-L1.

Specifically, the competitive ELISA was conducted as follows.

Step 3.1 Antigen Coating

A 96-well ELISA plate was coated with PD-1-mIgGFc antigen in a concentration of 0.5 µg/ml (50 µl per well) by incubation at 4° C. overnight.

Step 3.2 Blocking

After washed with the PBST buffer for three times and gently patted to dryness, the 96-well ELISA plate was blocked with 1% BSA in the PBS buffer at 37° C. for 2 hours, and washed with the 1×PBST buffer containing 1% Tween-20 for three times.

Step 3.3 Incubation with Primary Antibody

The antibody, secreted by the selected hybridoma cells, was diluted from 3 µg/ml in series by 1:3, with 7 gradient antibody solutions obtained. The 7 gradient antibody solutions and the blank PBS control (50 µl per well) were respectively added into the blocked 96-well ELISA plate for incubation at room temperature for 10 minutes.

Step 3.4 Incubation with Ligand

2 µg/ml of PDL1-hIgG1Fc solution in 50 µl per well was added for incubation at 37° C. for 1 hour.

Step 3.5 Incubation with Secondary Antibody

After the 96-well ELISA plate was washed with the PBST buffer for three times and gently patted to dryness, goat anti-mouse IgG-HRP (H+L) as a secondary antibody in 1:5000 dilution (50 µl per well) was added for incubation at 37° C. for 1 hour.

Step 3.6 Developing

After the 96-well ELISA plate was washed with the PBST buffer for three times and gently patted to dryness again, TMB as a developer in 50 µl per well was added for incubation at room temperature for 5 to 10 minutes.

Step 3.7 Termination of Developing

2M $H_2SO_4$ solution in 50 µl per well was added to terminate developing.

Step 3.8 Reading

The absorbance of solution in each well was measured with the microplate reader under a wavelength of 450 nm.

The PD-1 18A10 hybridoma cell line was selected out as the desired hybridoma cell line according to results, and the monoclonal antibody thereof is named as 18A10 antibody.

Step 4 Subcloning for Acquisition of Stable Cell Line

For the PD-1 18A10 hybridoma cell line obtained, subcloning is required to obtain a stable hybridoma cell line which secretes monoclonal antibodies competitively binding to PD-1 in the presence of PD-L1.

Specifically, the PD-1 18A10 hybridoma cell to be subcloned was counted, and then diluted with Iscove's modified Dubecco's medium (IMDM medium) containing 15% fetal bovine serum depending on the number of viable cells for seeding and incubation in a 96 well plate, a with theoretically seeding cell density of one cell per well. After grown into a monoclonal cell cluster, these cells were screened also by the ELISA method, followed by several repeats of subcloning and screening, thus obtaining the stable PD-1 18A10 hybridoma cell line.

Step 5 Production of 18A10 Antibody

The stable PD-1 18A10 hybridoma cell line was cultured with fetal bovine serum containing 10% IgG for 7 to 10 days, followed by collection of cell supernatant and purification to obtain the 18A10 antibody.

EXAMPLE 2

Acquisition of cDNA Sequence of 18A10 Hybridoma Cell Line 1. mRNA of the 18A10 hybridoma cell line was extracted according to the instruction of the RNAprep pure Cell/Bacteria Kit for total RNA extraction (Tiangen, Cat. No. DP430).

2. First strand of cDNA was synthesized according to the instruction of the Invitrogen SuperScript® III First-Strand Synthesis System for RT-PCR Kit, followed by PCR amplification.

3. The PCR amplified products were subjected to TA cloning according to the instruction of the pEASY-T1 Cloning Kit (Transgen, CT101).

4. The TA-cloned products were identified by PCR amplification with M13 universal primers, followed by selection of positive clones for sequencing.

5. By alignment, the accurate cDNA sequences was obtained from the sequencing results.

EXAMPLE 3

Design for Humanized 18A10 Antibody

In order to construct a humanized antibody, the sequences of the heavy chain variable region and the light chain variable region of murine 18A10 antibody were compared with the antibody germline sequences available in the public NCBI databases. Three humanized antibodies were designed by selectively mutating a part of the amino acid sequences of the murine 18A10 antibody to the corresponding human amino acid sequences, named as H1L1, H2L2 and H3L3 respectively according to the difference of humanization degree.

The heavy chain variable region of the humanized antibody H1L1 has a sequence of:

(SEQ ID NO: 1)
EVQLVQSGGGLVQPGGSLKLSCAASGFTFSSYGMSWVRQTPEKGLDWVA

TISGGGRDTYYPDSVKGRFTISRDNSKNNLYLQMNSLRAEDTALYYCAR

QKGEAWFAYWGQGTLVTVSS.

The light chain variable region of the humanized antibody H1L1 has a sequence of:

(SEQ ID NO: 2)
DIVLTQSPASLAVSPGQRATITCRASESVDNYGISFMNWFQQKPGQPPK

LLIYAASNKGTGVPARFSGSGSGTDFTLNIHPMEENDTAMYFCQQSKEV

PWTFGGGTKLEIK.

The heavy chain variable region of the humanized antibody H2L2 has a sequence of:

(SEQ ID NO: 3)
EVQLVQSGGGLVQPGGSLKLSCAASGFTFSSYGMSWVRQAPGKGLDWVA
TISGGGRDTYYPDSVKGRFTISRDNSKNNLYLQMNSLRAEDTALYYCAR
QKGEAWFAYWGQGTLVTVSS.

The light chain variable region of the humanized antibody H2L2 has a sequence of:

(SEQ ID NO: 4)
DIVLTQSPASLAVSPGQRATITCRASESVDNYGISFMNWFQQKPGQPPK
LLIYAASNKGTGVPARFSGSGSGTDFTLNINPMEENDTAMYFCQQSKEV
PWTFGGGTKLEIK.

The heavy chain variable region of the humanized antibody H3L3 has a sequence of:

(SEQ ID NO: 5)
EVQLVQSGGGLVQPGGSLKLSCAASGFTFSSYGMSWVRQAPGKGLDWVA
TISGGGRDTYYPDSVKGRFTISRDNSKNTLYLQMNSLRAEDTAVYYCAR
QKGEAWFAYWGQGTLVTVSS.

The light chain variable region of the humanized antibody H3L3 has a sequence of:

(SEQ ID NO: 6)
DIVLTQSPASLAVSPGQRATITCRASESVDNYGISFMNWYQQKPGQPPK
LLIYAASNKATGVPARFSGSGSGTDFTLNINPMEANDTAVYFCQQSKEV
PWTFGGGTKLEIK.

EXAMPLE 4

Expression of Humanized Antibodies H1L1, H2L2 and H3L3

The nucleic acid sequences encoding the humanized antibodies H1L1, H2L2, H3L3 were synthesized by the Gene Synthesis Method, and each was incorporated into an expression vector. DNAs of individual expression vectors were extracted, and transfected into mammalian 293 cells. After transfection, the antibody was expressed inside the cell and secreted out of the cell. After purification on the protein A affinity chromatography column, the humanized antibodies H1L1, H2L2 and H3L3 were obtained.

EXAMPLE 5

ELISA Experiments of Recombinant Humanized 18A10 Antibodies

The humanized antibodies, generated after acquisition of DNA sequence of 18A10 hybridoma cell line and humanization design by recombination technique, were assayed through a series of comparison experiments, including but not limited to ELISA binding experiment and competitive ELISA experiment.

1. ELISA binding experiments of 18A10 H1L1, 18A10 H2L2, and 18A10 H3L3 antibodies
Specifically, the ELISA binding experiments were conducted as follows.

Step 5.1.1 Antigen Coating
An ELISA plate was coated with PD-1-mFc antigen in a concentration of 0.5 μg/ml (50 μl per well) by incubation at 4° C. overnight.

Step 5.1.2 Blocking
The ELISA plate coated with the PD-1-mFc antigen was blocked with 1% BSA in the PBS buffer at 37° C. for 2 hours, and washed with 1×PBST buffer containing 1% Tween-20 for three times, with gently patting to dryness.

Step 5.1.3 Incubation with Primary Antibody
The 18A10 H1L1, 18A10 H2L2 and 18A10 H3L3 antibodies each were diluted from 1 μg/ml in series by 1:3, with 7 gradient antibody solutions obtained for each antibody. The 7 gradient antibody solutions for each antibody and the blank PBS control were respectively added into the blocked ELISA plate for incubation at 37° C. for 1 hour.

Step 5.1.4 Incubation with Secondary Antibody
After the ELISA plate was washed with the PBST buffer for three times and gently patted to dryness, goat anti-mouse IgG-HRP (H+L) as a secondary antibody in 1:5000 dilution (50 μl per well) was added for incubation at 37° C. for 1 hour.

Step 5.1.5 Developing
After the ELISA plate was washed with the PBST buffer for three times and gently patted to dryness again, TMB as a developer in 50 μl per well was added for incubation at room temperature for 5 to 10 minutes.

Step 5.1.6 Termination of Developing
2M $H_2SO_4$ solution in 50 μl per well was added to terminate developing.

Step 5.1.7 Reading
The absorbance of solution in each well was measured with the microplate reader under a wavelength of 450 nm.
The results are shown in FIG. 1, from which the $EC_{50}$ values of the H1L1, H2L2 and H3L3 antibodies against PD-1 are 0.156 nM, 0.111 nM and 0.144 nM, respectively.
It can be seen from FIG. 1 that the H1L1, H2L2 and H3L3 antibodies each have strong affinity for PD-1.

TABLE 1

| Dilution of antibody | 18A10 H1L1 | | 18A10 H2L2 | | 18A10 H3L3 | |
|---|---|---|---|---|---|---|
| 1 μg/ml | 2.468 | 2.323 | 2.359 | 2.434 | 2.139 | 2.435 |
| 1:3 | 2.347 | 2.342 | 2.132 | 2.358 | 2.286 | 2.091 |
| 1:9 | 1.960 | 1.978 | 2.180 | 1.978 | 1.954 | 2.056 |
| 1:27 | 1.620 | 1.650 | 1.778 | 1.631 | 1.584 | 1.503 |
| 1:81 | 0.883 | 0.834 | 1.036 | 1.139 | 0.928 | 0.809 |
| 1:243 | 0.450 | 0.431 | 0.545 | 0.475 | 0.432 | 0.377 |
| 1:729 | 0.186 | 0.163 | 0.226 | 0.224 | 0.200 | 0.185 |
| 0 | 0.074 | 0.078 | 0.064 | 0.070 | 0.067 | 0.039 |

2 Competitive ELISA experiments of 18A10 H1L1, 18A10 H2L2 and 18A10 H3L3 antibodies with PDL1
Specifically, the competitive ELISA experiments were conducted as follows.

Step 5.2.1 Antigen Coating
A 96-well ELISA plate was coated with PD-1-mIgGFc antigen in a concentration of 0.5 μg/ml (50 μl per well) by incubation at 4° C. overnight.

Step 5.2.2 Blocking
After washed with the PBST buffer for three times and gently patted to dryness, the 96-well ELISA plate was blocked with 1% BSA in the PBS buffer at 37° C. for 2 hours, and washed with 1×PBST buffer containing 1% Tween-20 for three times.

Step 5.2.3 Incubation with Primary Antibody
The 18A10 H1L1, 18A10 H2L2 and 18A10 H3L3 antibodies each were diluted from 3 μg/ml in series by 1:3, with 7 gradient antibody solutions obtained for each antibody. The 7 gradient antibody solutions for each antibody and the blank PBS control (50 μl per well) were respectively added into the blocked 96-well ELISA plate for incubation at room temperature for 10 minutes.

Step 5.2.4 Incubation with Ligand 0.3 μg/ml of PDL1-mIgG2aFc solution in 50 μl per well was added for incubation at 37° C. for 1 hour.

Step 5.2.5 Incubation with Secondary Antibody

After the 96-well ELISA plate was washed with the PBST buffer for three times and gently patted to dryness, goat anti-mouse IgG-HRP (H+L) as a secondary antibody in 1:5000 dilution (50 μl per well) was added for incubation at 37° C. for 1 hour.

Step 5.2.6 Developing

After the 96-well ELISA plate was washed with the PBST buffer for three times and gently patted to dryness again, TMB as a developer in 50 μl per well was added for incubation at room temperature for 5 to 10 minutes.

Step 5.2.7 Termination of Developing

2M $H_2SO_4$ solution in 50 μl per well was added to terminate developing.

Step 5.2.8 Reading

The absorbance of solution in each well was measured with the microplate reader under a wavelength of 450 nm.

Figure 2:
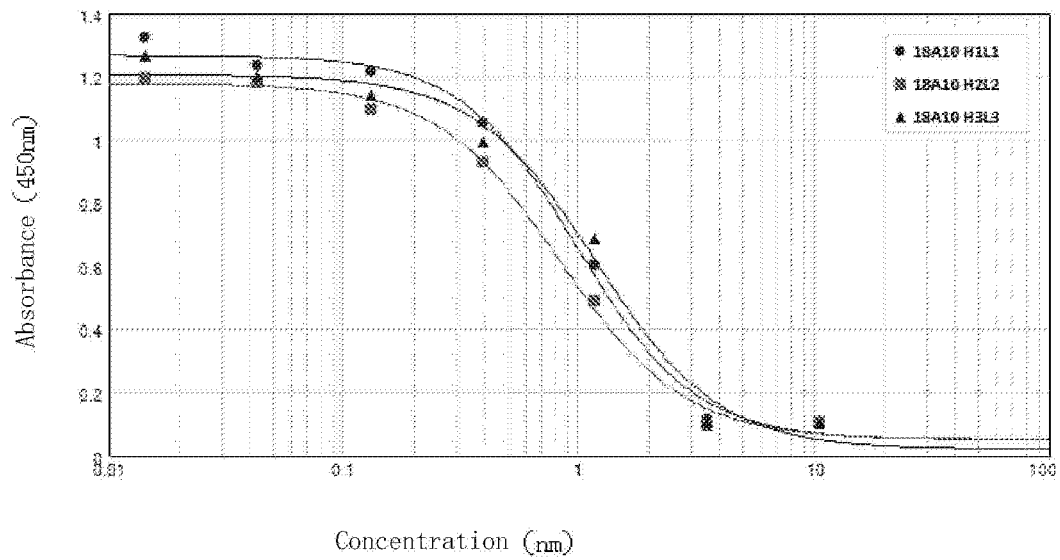
FIG. 2 is a graph showing competitive ELISA results of H1L1, H2L2 and H3L3 antibodies competing with PdL1 on binding PD-1 according to an embodiment of the present disclosure.

The results are shown in FIG. 2, from which the $EC_{50}$ values of the H1L1, H2L2 and H3L3 antibodies when competing with PdL1 on binding PD-1 are 0.992 nM, 0.838 nM and 1.194 nM respectively.

It can be seen from FIG. 2 that the H1L1, H2L2 and H3L3 antibodies each are capable of inhibiting the binding of Pd-1 to PdL1 effectively.

TABLE 2

| Dilution of antibody | 18A10 H1L1 | | 18A10 H2L2 | | 18A10 H3L3 | |
|---|---|---|---|---|---|---|
| 1.5 μg/ml | 0.110 | 0.107 | 0.110 | 0.102 | 0.101 | 0.102 |
| 1:3 | 0.123 | 0.109 | 0.097 | 0.097 | 0.103 | 0.108 |
| 1:9 | 0.625 | 0.586 | 0.474 | 0.506 | 0.700 | 0.678 |
| 1:27 | 1.062 | 1.039 | 0.951 | 0.903 | 1.002 | 0.986 |
| 1:81 | 1.293 | 1.136 | 1.095 | 1.100 | 1.093 | 1.194 |
| 1:243 | 1.258 | 1.210 | 1.158 | 1.208 | 1.197 | 1.207 |
| 1:729 | 1.347 | 1.296 | 1.199 | 1.191 | 1.283 | 1.243 |
| 0 | 1.378 | 1.312 | 1.263 | 1.291 | 1.255 | 1.369 |
| Ligand | PDL1-mIgG2aFc 0.3 μg/ml | | | | | |

3 Competitive ELISA Experiment of 18A10 H2L2 Antibody with PDL2

Specifically, the competitive ELISA experiment was conducted as follows.

Step 5.3.1 Antigen Coating

A 96-well ELISA plate was coated with PD-1-hIgGFc antigen in a concentration of 1μg/ml (100 μl per well) by incubation at 4° C. overnight.

Step 5.3.2 Blocking

After washed with the PBST buffer for three times and gently patted to dryness, the 96-well ELISA plate was blocked with 1% BSA in the PBS buffer at 37° C. for 2 hours, and washed with 1×PBST buffer containing 1% Tween-20 for four times.

Step 5.3.3 Incubation with Primary Antibody

The 18A10 H2L2 antibody was diluted from 20 μg/ml in series by 1:3, with 7 gradient antibody solutions obtained. The 7 gradient antibody solutions and the blank PBS control (50 μl per well) were respectively added into the blocked 96-well ELISA plate for incubation at room temperature for 10 minutes.

Step 5.3.4 Incubation with Ligand 1.0 μg/ml of PDL2-his tag solution in 50 μl per well was added for incubation at 37° C. for 1 hour.

Step 5.3.5 Incubation with Secondary Antibody

After the 96-well ELISA plate was washed with the PBST buffer for five times and gently patted to dryness, HRP conjugated anti-his tag mouse monoclonal antibody as a secondary antibody in 1:750 dilution (50 μl per well) was added for incubation at 37° C. for 1 hour.

Step 5.3.6 Developing

After the 96-well ELISA plate was washed with the PBST buffer for six times and gently patted to dryness again, TMB as a developer in 100 μl per well was added for incubation at room temperature for 30 minutes.

Step 5.3.7 Termination of Developing

2M $H_2SO_4$ solution in 50 μl per well was added to terminate developing.

Step 5.3.8 Reading

The absorbance of solution in each well was measured with the microplate reader under a wavelength of 450 nm.

Figure 3:
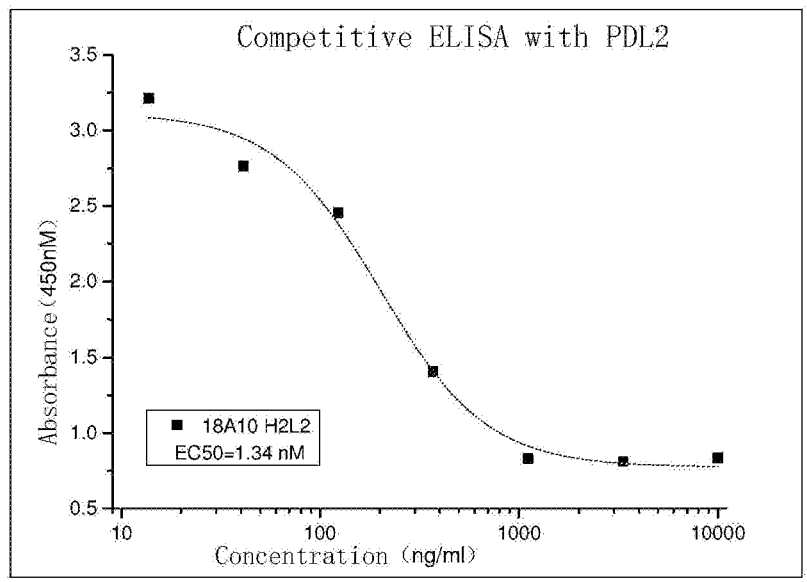
FIG. 3 is a graph showing competitive ELISA results of H2L2 antibody competing with PdL2 on binding PD-1 according to an embodiment of the present disclosure.

The results are shown in FIG. 3, from which it can be seen that the H2L2 antibody is capable of inhibiting the binding of PD-1 to PdL2 effectively.

TABLE 3

| Dilution of antibody | 18A10 H2L2 | |
|---|---|---|
| 10 μg/ml | 0.876 | 0.792 |
| 1:3 | 0.821 | 0.803 |
| 1:9 | 0.865 | 0.793 |
| 1:27 | 1.431 | 1.385 |
| 1:81 | 2.654 | 2.251 |
| 1:243 | 2.624 | 2.904 |
| 1:729 | 3.24 | 3.185 |
| Blank | 0.401 | 0.28 |
| Ligand | PDL2-his tag 0.5 μg/ml | |

EXAMPLE 6

Kinetic characteristic parameters of 18A10 H1L1, H2L2 and H3L3 antibodies were determined using the Fortebio molecule interaction instrument.

Figure 4:
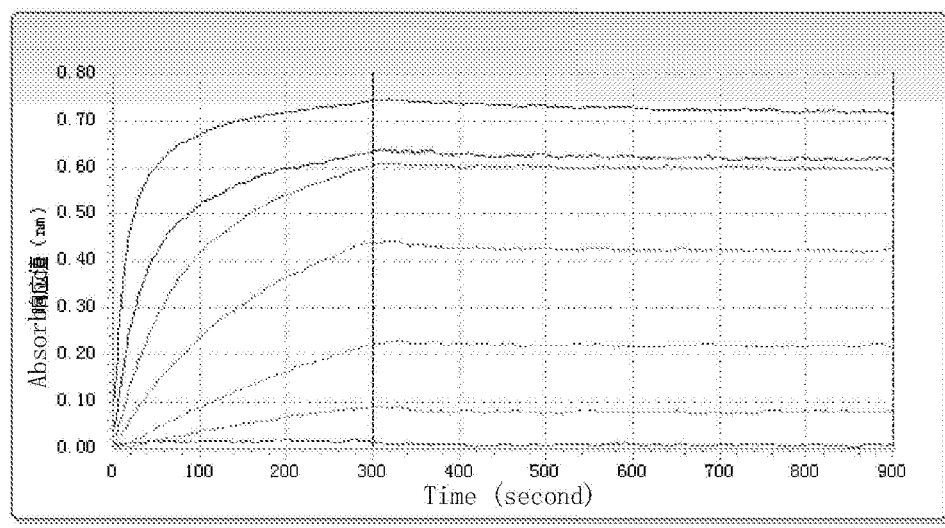
FIG. 4 is a graph showing the dynamic characteristic parameters of H1L1 antibody according to an embodiment of the present disclosure.
Figure 5:
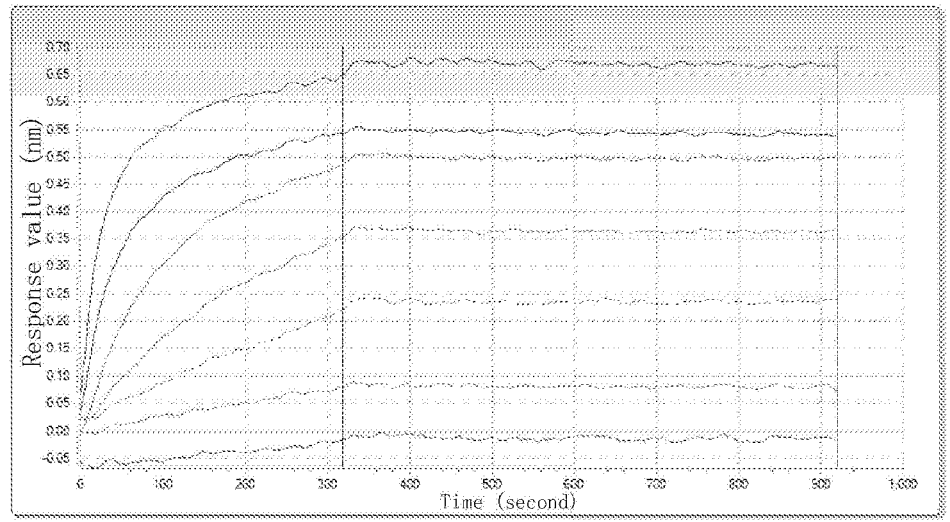
FIG. 5 is a graph showing the dynamic characteristic parameters of H2L2 antibody according to an embodiment of the present disclosure.
Figure 6:
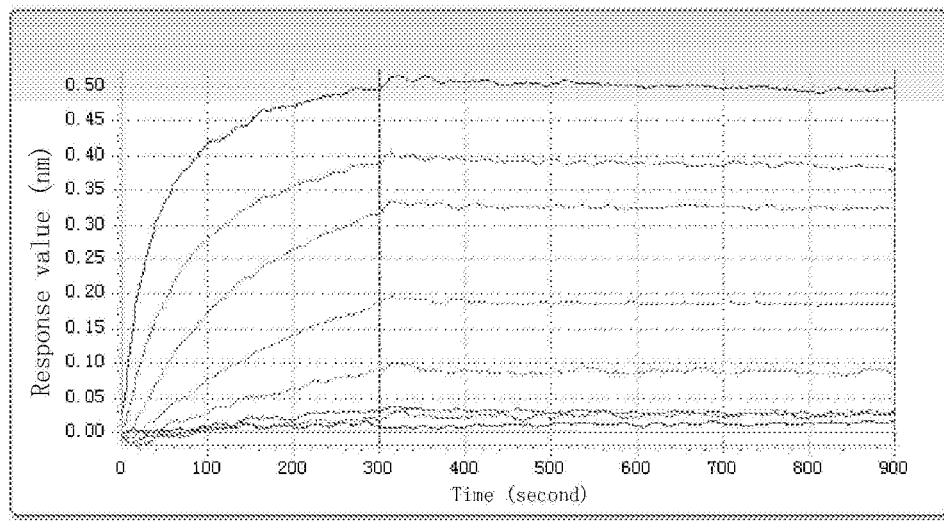
FIG. 6 is a graph showing the dynamic characteristic parameters of H3L3 antibody according to an embodiment of the present disclosure.

The biotin-labeled PD-1 antigen was immobilized on the surface of the SA sensor. After equilibration with the PBST buffer, the H1L1 antibody, diluted in series by 1:3 with PBST (200 nM, 66.67 nM, 22.22 nM, 7.41 nM, 2.47 nM, 0.82 nM, 0.27 nM and 0 nM), was applied to the SA sensor for binding to the biotin-labeled PD-1 antigen, after which PBST was applied to the SA sensor for disassociation. Assays for H2L2 and H3L3 are the same as H1L1. Results of kinetic characteristic parameters of the H1L1, H2L2 and H3L3 antibodies are shown in Table 4, FIG. 4, FIG. 5 and FIG. 6.

TABLE 4

| Antibody name | $K_D$ (M) | $K_{on}$ (1/Ms) | $K_{on}$ Error | $K_{dis}$ (1/s) | $K_{dis}$ Error | Rmax Range |
|---|---|---|---|---|---|---|
| H1L1 | 3.60E−11 | 3.67E+05 | 7.28E+03 | 1.32E−05 | 8.12E−06 | 0.6192-0.9442 |
| H2L2 | 4.28E−11 | 2.31E+05 | 6.11E+03 | 9.86E−06 | 1.12E−05 | 0.5382-1.3794 |
| H3L3 | 1.14E−10 | 1.37E+05 | 2.41E+03 | 1.56E−05 | 7.97E−06 | 0.4226-0.9384 |

EXAMPLE 7

Assays of IL-2 and IFN Gamma Secreted by T Cells Under Stimulation of H1L1, H2L2 and H3L3 Antibodies T lymphocytes were assayed for IL-2 and IFN gamma secretion under stimulation of H1L1, H2L2 and H3L3 antibodies by the mixed lymphocyte reaction (MLR). For MLR, T cells (TC) and dendritic cells (DC) from different human sources were mixed, such that the T cells secrete IL-2 and IFN gamma under antigen presenting function of the DC cells. Specifically, monocytes in the blood differentiate into immature DC cells under the induction of cytokines GM-CSF and IL-4, after which the immature DC cells were induced to maturation via stimulation of tumor necrosis factor alpha (TNFα). Subsequently, the matured DC cells and allogeneic TC cells are mixed and cultured for 5 days, thereafter the secreted IL-2 and IFN gamma in cell supernatant were determined.

In this example, the TC cells ($1 \times 10^5$ per well) and the matured DC cells ($1 \times 10^4$ per well) were mixed in a 96 well plate, and then cultured in the presence of individual antibodies in three concentrations (i.e. 1 nM, 10 nM and 100 nM) for 5 days, after which the amount of IL-2 in cell supernatant was detected with an IL-2 assay kit, and the amount of IFN gamma in the cell supernatant was detected with an IFN gamma assay kit.

Figure 7:
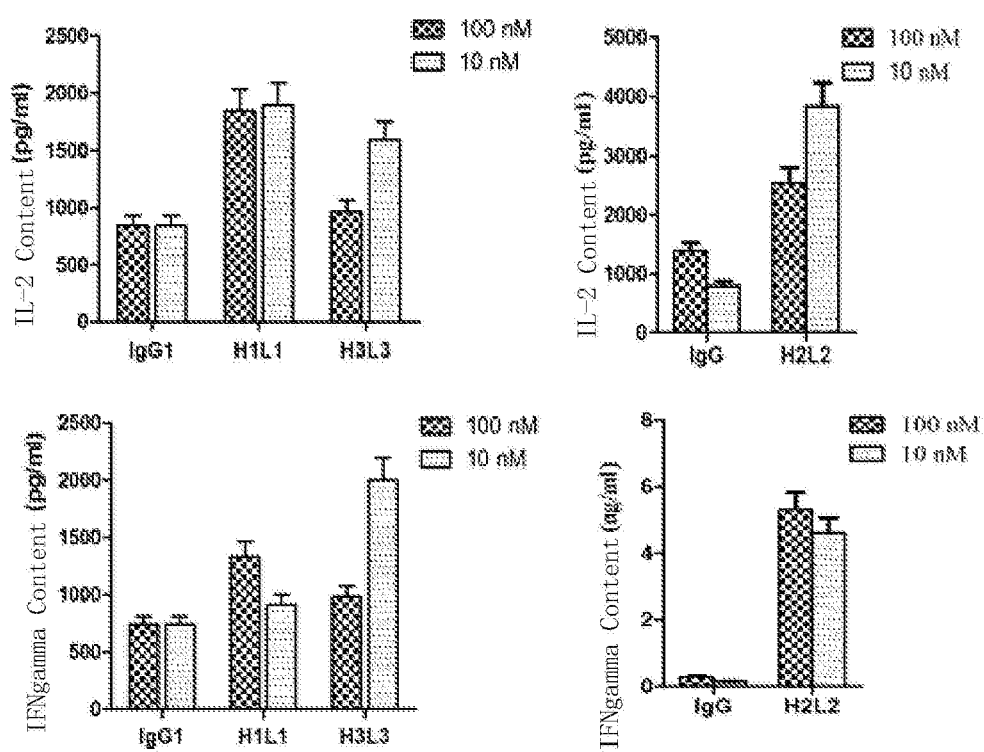
FIG. 7 is a graph showing contents of IL-2 and IFN gamma secreted by T cells under stimulation of H1L1, H2L2 and H3L3 antibodies via blocking the activation of PD-1 protein according to an embodiment of the present disclosure.

FIG. 7 shows contents of IL-2 and IFN gamma secreted by T cells under the stimulation of the H1L1, H2L2 and H3L3 antibodies respectively, from which it can be seen that the H1L1, H2L2 and H3L3 antibodies are capable of stimulating T cells to secrete IL-2 and IFN gamma in an effective and dose-dependent manner.

EXAMPLE 8

Assay of EC50 of H1L1, H2L2 and H3L3 antibodies binding to PD-1

The binding efficiencies of H1L1, H2L2 and H3L3 antibodies to PD-1 antigen stably expressed on the surface of cells (named as BB007 cells) were determined by flow cytometry. The BB007 cells were obtained by routine trypsin digestion, and then washed with PBS buffer once, followed by dividing into several tubes, with $2 \times 10^5$ cells per tube. After dilution into concentrations of 20 nM, 10 nM, 5 nM, 1 nM, 0.1 nM and 0 nM with the PBS buffer containing 1% BSA for each of the H1L1, H2L2 and H3L3 antibodies, individual antibodies in a volume of 100 μl were added into individual tubes and incubated on ice for 1 hour. After the mixture was washed with the PBS buffer once, 100 μl FITC-Goat-Anti-Human IgG (in 1:500 dilution) was added for each tube and incubated on ice for 1 hour, followed by addition of 300 μl the PBS buffer for detecting fluorescence signal with a FITC channel on the flow cytometer.

Figure 8:
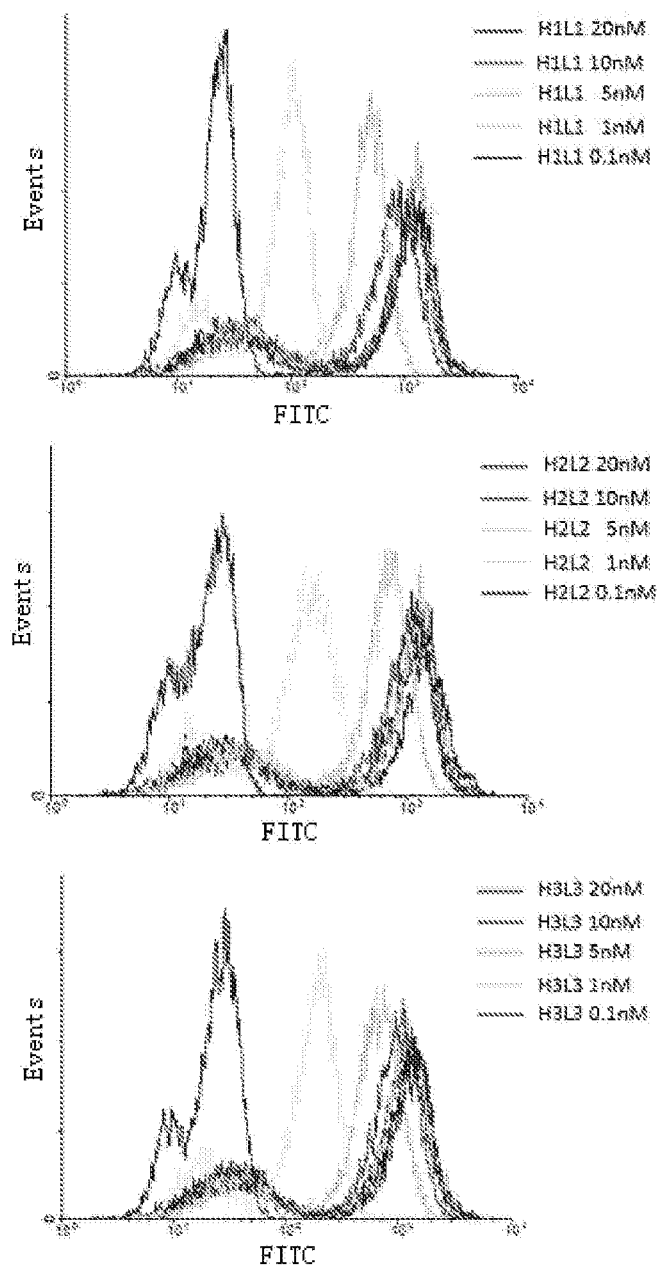
FIG. 8 is a graph showing fluorescence of H1L1, H2L2 and H3L3 antibodies binding to BB007 cells according to an embodiment of the present disclosure.

Table 5 shows the binding efficiencies of the H1L1, H2L2 and H3L3 antibodies to the BB007 cell. It can be seen from FIG. 8 that the H1L1, H2L2 and H3L3 antibodies are capable of binding to the target protein PD-1 on the surface of the BB007 cell, and the binding efficiencies thereof are in a dose-dependent relationship.

Table 5 fluorescence intensities of H1L1, H2L2 and H3L3 antibodies after binding to BB007 cells

| (nM) | fluorescence intensity | | | | | | EC50 |
|---|---|---|---|---|---|---|---|
| | 0 | 0.1 | 1 | 5 | 10 | 20 | |
| hIgG | 7.4 | | | | | | |
| H1L1 | | 18.96 | 64.4 | 252.42 | 316.13 | 358.13 | 3.38 nM |
| H2L2 | | 19.09 | 92.55 | 320.89 | 349.07 | 329.08 | 1.59 nM |
| H3L3 | | 21.18 | 110.34 | 342.71 | 386.38 | 366.73 | 1.68 nM |

Figure 9:
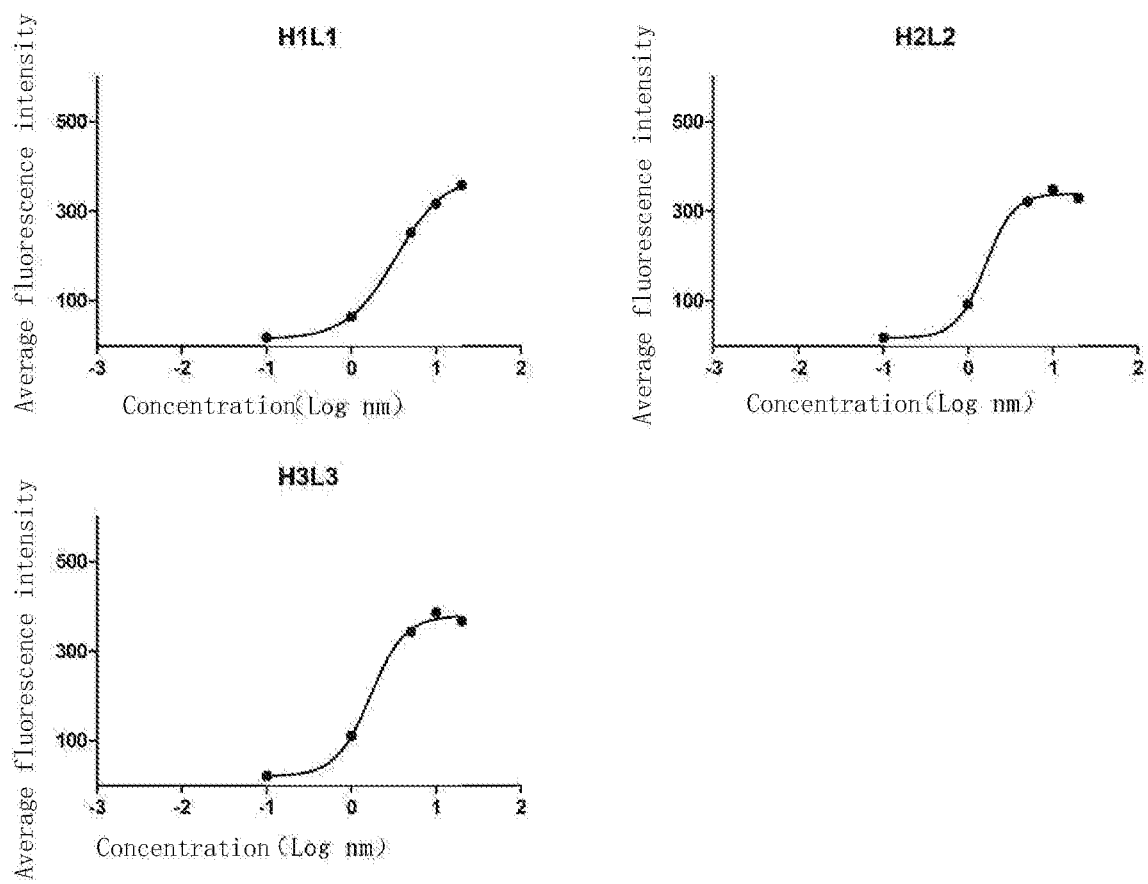
FIG. 9 is a graph showing fluorescence intensities of H1L1, H2L2 and H3L3 antibodies binding to BB007 cells according to an embodiment of the present disclosure.

After quantitative fluorescence analysis on the H1L1, H2L2 and H3L3 antibodies binding to BB007 cell, the EC50 values (indicating binding efficiency) obtained by curve simulation for the H1L1, H2L2 and H3L3 antibodies are 3.38 nM, 1.59 nM and 1.68 nM respectively (FIG. 9).

In the specification of the present disclosure, the terms "an embodiment", "some embodiments", "an example", "a specific example", "some examples" and the like are intended to refer to particular features, structures, materials or characteristics described by way of example or embodiment are contained in at least one embodiment or example of the disclosure. In this specification, the schematic representation of the above terms does not necessarily refer to the same embodiment or example. Moreover, the particular features, structures, materials or characteristics described may be combined in any suitable manner in one or more embodiments or examples. In addition, various embodiments or examples described in the specification, as well as features of such the embodiments or examples, may be combined by those skilled in the art without conflict.

Although embodiments of the present disclosure have been described, it will be understood by those skilled in the art that such the embodiments are explanatory and should not be construed to limit the present disclosure. Further, various changes, modifications, substitutions and variations can be made in these embodiments by those skilled in the art without departing from the scope of the present disclosure.

What is claimed is:

1. An antibody or antigen-binding fragment thereof, comprising:
   a heavy chain CDR1 comprising the amino acid sequence of GFTFSSYG (SEQ ID NO:14), CDR2 comprising the amino acid sequence of ISGGGRDT (SEQ ID NO:15), and CDR3 comprising the amino acid sequence of ARQKGEAWFAY (SEQ ID NO:16); and
   a light chain CDR1 comprising the amino acid sequence of ESVDNYGISF (SEQ ID NO:17), CDR2 comprising the amino acid sequence of AAS (SEQ ID NO:18), and CDR3 comprising the amino acid sequence of QQSKEVPWT (SEQ ID NO:19).

2. The antibody or antigen-binding fragment thereof according to claim 1, comprising a heavy chain variable region comprising the amino acid sequence of SEQ ID NO: 1, 3, or 5.

3. The antibody or antigen-binding fragment thereof according to claim 1, comprising a light chain variable region comprising the amino acid sequence of SEQ ID NO: 2, 4, or 6.

4. The antibody or antigen-binding fragment thereof according to claim 1, comprising:
   a heavy chain variable region comprising the amino acid sequence of SEQ ID NO: 1 and a light chain variable region comprising the amino acid sequence of SEQ ID NO: 2;
   a heavy chain variable region comprising the amino acid sequence of SEQ ID NO: 3 and a light chain variable region comprising the amino acid sequence of SEQ ID NO: 4; or
   a heavy chain variable region comprising the amino acid sequence of SEQ ID NO: 5 and a light chain variable region comprising the amino acid sequence of SEQ ID NO: 6.

5. The antibody or antigen-binding fragment thereof according to claim 1, wherein the antibody or antigen-binding fragment thereof is humanized.

6. The antibody or antigen-binding fragment thereof according to claim 1, comprising:
   a heavy chain variable region comprising the amino acid sequence of SEQ ID NO:3, and
   a light chain variable region comprising the amino acid sequence of SEQ ID NO:4.

* * * * *